(12) United States Patent
Hartman et al.

(10) Patent No.: US 8,220,504 B2
(45) Date of Patent: *Jul. 17, 2012

(54) PERISTALTIC SYRINGE FILLING STATION

(75) Inventors: Steven Hartman, Commack, NY (US); Alan Cross-Hansen, Massapequa Park, NY (US); Clark Godfrey, East Northport, NY (US); Robert C. Williams, Fort Salonga, NY (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 221 days.

This patent is subject to a terminal disclaimer.

(21) Appl. No.: 12/720,291

(22) Filed: Mar. 9, 2010

(65) Prior Publication Data

US 2011/0061765 A1 Mar. 17, 2011

Related U.S. Application Data

(63) Continuation of application No. 10/559,298, filed as application No. PCT/US2004/017802 on Jun. 4, 2004, now Pat. No. 7,703,483.

(60) Provisional application No. 60/476,578, filed on Jun. 6, 2003.

(51) Int. Cl.
*B65B 1/04* (2006.01)
(52) U.S. Cl. .................................................. 141/27
(58) Field of Classification Search ............... 141/2, 18, 141/21, 27, 67, 98; 604/416
See application file for complete search history.

(56) References Cited

U.S. PATENT DOCUMENTS

| 1,083,183 | A | 12/1913 | Bednarowicz |
| 3,661,189 | A | 5/1972 | Bowser et al. |
| 3,844,318 | A | 10/1974 | Raia et al. |
| 3,935,883 | A | 2/1976 | Stach et al. |
| 3,965,945 | A | 6/1976 | Ross |
| 4,489,766 | A | 12/1984 | Montada |

(Continued)

FOREIGN PATENT DOCUMENTS

JP 09-103484 4/1997

(Continued)

OTHER PUBLICATIONS

Japanese Office Action corresponding to JP 2006-515209 dated Oct. 24, 2008.

*Primary Examiner* — Steven Douglas
(74) *Attorney, Agent, or Firm* — Fredrikson & Byron, P.A.

(57) ABSTRACT

The present invention is directed to a syringe filling station that can fill a syringe with a specified volume of fluid. In one embodiment, the syringe filling station comprises a reservoir attachment, a fluid delivery system, a syringe retaining guide, and a pump to move fluid from a reservoir to a syringe. The fluid delivery system may comprise a sterile consumable cartridge that is insertable into the filling station and defines a fluid pathway from a reservoir to a syringe. The syringe filling station may also include a user interface. An operator can input commands into the user interface to specify the amount of fluid to dispense into the syringe. The user interface may be connected to a processor that controls the rate of pumping and thereby can fill a syringe with a desired amount of fluid. The filling station may also include sensors that detect air in the tubing, depletion of the reservoir, among other things.

20 Claims, 11 Drawing Sheets

U.S. PATENT DOCUMENTS

| | | | |
|---|---|---|---|
| 4,883,101 A | 11/1989 | Strong | |
| 4,976,590 A | 12/1990 | Baldwin | |
| 5,012,845 A | 5/1991 | Averette | |
| 5,220,949 A | 6/1993 | Rufenacht | |
| 5,292,318 A | 3/1994 | Haber et al. | |
| 5,304,165 A | 4/1994 | Haber et al. | |
| 5,329,976 A | 7/1994 | Haber et al. | |
| 5,385,559 A | 1/1995 | Mannix | |
| 5,487,738 A | 1/1996 | Sciulli | |
| 5,647,409 A | 7/1997 | Christ et al. | |
| 5,832,972 A | 11/1998 | Thomas et al. | |
| 5,911,252 A | 6/1999 | Cassel | |
| 6,155,312 A | 12/2000 | Bosy | |
| 6,286,566 B1 | 9/2001 | Cline et al. | |
| 6,488,650 B1 | 12/2002 | Epstein et al. | |
| 6,733,477 B2 | 5/2004 | Cowan et al. | |
| 6,915,823 B2 * | 7/2005 | Osborne et al. | 141/27 |

FOREIGN PATENT DOCUMENTS

| | | |
|---|---|---|
| JP | 10-509358 | 9/1998 |
| JP | 11-035001 | 2/1999 |
| JP | 2000-506425 | 5/2000 |
| JP | 20002-326607 | 11/2002 |
| WO | WO 96/14099 | 5/1996 |
| WO | WO 98/25570 | 6/1998 |

* cited by examiner

PERISTALTIC SYRINGE FILLING STATION

CROSS REFERENCE TO RELATED APPLICATION

This application is a continuation of U.S. patent application Ser. No. 10/559,298, filed May 5, 2006, now U.S. Pat. No. 7,703,483, which is a national phase of PCT/US2004/017802 filed Jun. 4, 2004, which claims the benefit of Provisional Application No. 60/476,578 filed Jun. 6, 2003, each of which is hereby incorporated herein in its entirety by reference.

FIELD OF THE INVENTION

The invention relates generally to the field of syringe filling, and more particularly to a method and apparatus for peristaltic syringe filling.

BACKGROUND OF THE INVENTION

Many medical procedures require injecting a fluid into a patient using a syringe. In particular, medical fluid injection systems, such as a CT injector uses one or more syringes to inject a measured amount of a fluid into a patient. Before the syringes can be used to inject a fluid, they must first be filled with a fluid. In some instances, filling a syringe may be inexact, inconvenient, and inflexible.

One method of obtaining a loaded syringe is to purchase a syringe that has been pre-loaded with the desired fluid. However, this method has several disadvantages. First, pre-loaded syringes having the desired fluid may not be readily available. Second, if the syringe is available, it may not have the desired amount of fluid. For these and other reasons, pre-loaded syringes may not be desirable.

An alternative method of filling syringes involve connecting an empty syringe to a supply reservoir via a tubing. The syringe plunger is manually withdrawn from the syringe barrel. As the plunger is withdrawn, fluid within the reservoir is drawn into the syringe. This method provides greater flexibility in fluid type and in the amount to be pre-loaded in the syringe. Here, the operator must "eye-ball" the amount of fluid that has entered the syringe to determine when a desired amount of fluid has been transferred to the syringe. Here, the accuracy of the fluid being transferred is dependant on the skill and care of the operator. Additionally, it may be difficult to completely fill the syringe because of air trapped in the tubing. It may also be difficult in forming a necessary vacuum to draw fluid into the syringe. Further, mutually drawing fluid into the barrel may afford the possibility of contamination inside the syringe because the entire reservoir is not utilized to fill the syringe.

SUMMARY OF THE INVENTION

In one alternative embodiment, the invention is a syringe filling station that can fill a syringe with a substantially accurate amount of fluid medium. Further, the filling station may be a completely enclosed system that can be easily operated with a single hand. Also, the filling station may be used with a wide variety of fluids such as a contrast medium or flushing fluid.

In one alternative embodiment of the present invention, the syringe filling station comprises a reservoir attachment, a fluid delivery system, a syringe retaining guide, and a pump to move fluid from a reservoir to a syringe. In one embodiment, the fluid delivery system may be a sterile consumable cartridge that is insertable into the filling station and defines a fluid pathway from a reservoir to a syringe. The fluid delivery system may also include a flexible tubing attached to a spike at one end, and a canula at the other. The spike may be inserted into a reservoir and the canula may be at least partially inserted into a syringe. The tubing can be threaded through the syringe filling station and brought into close proximity with the pump. In one embodiment, rotation of the pump moves fluid through the tubing.

The syringe filling station can also include a user interface. In one embodiment, an operator can input commands into the user interface to specify an amount of fluid that is to be dispensed into the syringe. The user interface can be connected to a processor controlling the rate of pumping to accurately fill a syringe with a desired amount of fluid. The filling station can also include sensors that will detect air in the tubing, depletion of the reservoirs, and the like. The sensors can send signals to the processor. The processor in turn, can direct the pump to carry out certain functions depending upon the data received from the sensors. As a result, the filling station can be used to efficiently and accurately fill syringes with a desired amount of fluid.

In one embodiment, the disposable administration cartridge is available in a pre-assembled state so that it can easily be positioned and disposed within the syringe filling station. The administration cartridge helps to ensure that an aseptic or sterile interface is maintained between the reservoir and spike, and between the canula and syringe. The syringe filling station can also include a clear plastic window through which an operator can view the syringe as it is inserted into the syringe retaining guide. As a result, the syringe filling station provides an aseptic or sterile environment for filling a syringe with a medical fluid.

The invention also includes a method of using the syringe filling station. In one embodiment of the invention, the invention comprises the steps of: a) providing a filling station having a reservoir attachment for removably receiving a reservoir, a fluid pump, and a syringe retaining guide; b) providing a fluid delivery system having a projecting member, a canula, and a flexible tubing; c) installing the fluid delivery system into the filling station to define a fluid pathway from the reservoir attachment to the syringe retaining guide; d) connecting a fluid reservoir to the reservoir attachment; e) inserting a syringe into the retaining guide so that at least a portion of the canula is partially inserted into the syringe; and f) pumping the fluid from the reservoir into the syringe.

Thus, among other things, the invention provides an efficient and reliable apparatus and method for filling a syringe with a fluid. Other objects, features, and advantages of the present invention will be apparent to those of ordinary skill in the art in view of the following detailed description of the invention and the accompanying drawings.

BRIEF DESCRIPTION OF THE SEVERAL VIEWS OF THE DRAWING(S)

Having thus described the invention in general terms, reference will now be made to the accompanying non-limiting drawings, which are not necessarily drawn to scale:

DETAILED DESCRIPTION OF THE INVENTION

The present invention now will be described more fully hereinafter with reference to the accompanying drawings. Indeed, the invention may be embodied in many different forms and should not be construed as limited to the embodiments set forth herein; rather, these embodiments are provided for illustrative purposes only.

In one embodiment, the invention is a syringe filling station that can fill a syringe with a selected or predetermined amount of fluid. The station may include a reservoir outlet for receiving a reservoir; a syringe retaining guide for releasably receiving and securing a syringe; a fluid delivery system defining a fluid path between the reservoir and the syringe; and a pump for moving the fluid from the reservoir to the syringe. In one preferred embodiment, the syringe filling station includes a user interface to input and control the amount of fluid that is delivered to the syringe.

The reservoir can contain fluids that are useful in the medical field, such as a contrast medium. The term "contrast medium" refers generally to any suitable medium that is typically used in the medical field and that can be injected into a patient or subject to highlight selected areas of the patient's body while he/she is being, for example, radiographically scanned. Typically, a contrast medium is used in conjunction with an imaging device to perform medical diagnostic imaging such as CT scans, MRI, ultrasound, etc. Other media that can be used with the injector include, but are not limited to, saline media, flush media, and the like. The filling station in some embodiments is particularly useful for filling syringes with Newtonian flow fluids having viscosities that are typically up to about 100 cps. Typically, the viscosity is from about 0.5 to 100 cps, and preferably from about 1 to 50 cps.

In one exemplary embodiment, the present invention is a device for delivering a fluid into a syringe. The device comprises a reservoir attachment for removably receiving a reservoir having a fluid; a syringe retaining guide for releasably securing a syringe; a consumable administration cartridge defining a fluid pathway between a reservoir and a syringe; and a pump for pumping a fluid from a reservoir through the administration cartridge and into a syringe. The administration cartridge comprises a projecting member for inserting into a reservoir, a flexible tubing having a distal end attached to the projecting member, and a canula attached to the proximal end of the flexible tubing that is adapted for at least partial insertion into a syringe. Preferably, the administration cartridge is available as a unitary cartridge wherein the projecting member, canula, and spike are preassembled for easy installation into the filling station.

In an alternative exemplary embodiment, the invention is a syringe filling station comprising a reservoir having a fluid medium; a fluid delivery system having a projecting member inserted into the reservoir, a flexible tubing having a distal end attached to the projecting member, and a canula attached to the proximal end of the flexible tubing; a syringe having a generally elongated body and a passageway disposed near the discharge region of the syringe, wherein the canula is extending into the passageway so that fluid can be delivered from the reservoir into the syringe; a pump for pumping the fluid from the reservoir into the syringe; and a control unit that is operatively connected to the pump, whereby the control unit can control the pump so that a specific volume of fluid is dispensed into the syringe.

Figure 1:
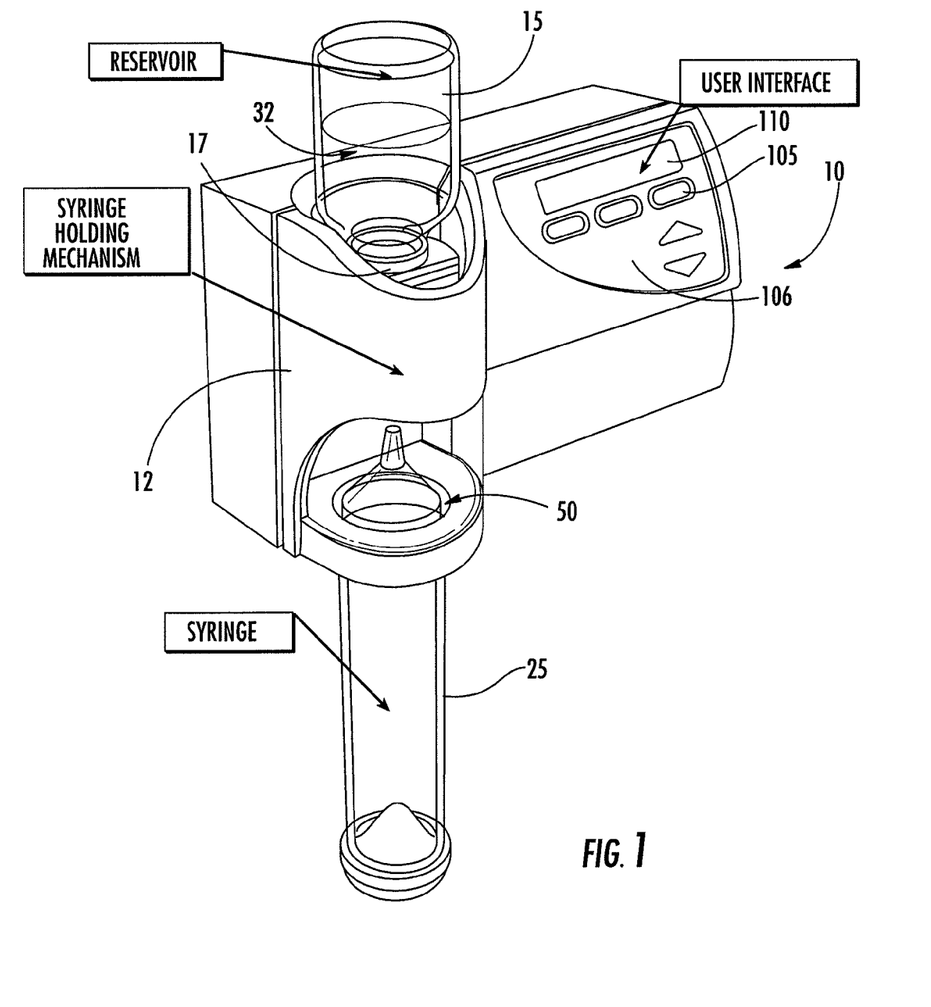
FIG. 1 is an exemplary graphical illustration of a syringe filling station of the present invention.

With reference to FIG. 1, an exemplary syringe filling station is broadly designated with reference number 10. The syringe filling station 10 may include a housing 12 containing a fluid pump (not shown), a reservoir attachment 17, and a syringe retaining guide 50. The reservoir attachment can be adapted for removably receiving the reservoir 15. A syringe retaining lock or guide can be used to guide and securely position the syringe 25 within the housing 12. In some embodiments, the housing can include a clear viewing window 11 that serves as a visualization aid in assuring that the operator has correctly inserted and attached a syringe. The clear viewing window 11 provides a partial barrier to possible routes of airborne contamination to the tip of a syringe that is disposed in the housing. A fluid delivery system (not shown) defines a fluid path from the reservoir to the syringe. The filling station can also include a user interface 106 having a digital display 110 and touch controls 105 to input syringe filling commands, such as stop, pause, purge line, fill volume, for example.

The syringe filling station as depicted in FIG. 1 can be a totally or partially enclosed unit that can be wall-mounted or positioned on a tabletop. The syringe filling station provides a sterile mechanism or conduit for delivering a sterile fluid through a sterile pathway to the interior of a syringe, which may also be sterile.

Figure 2:
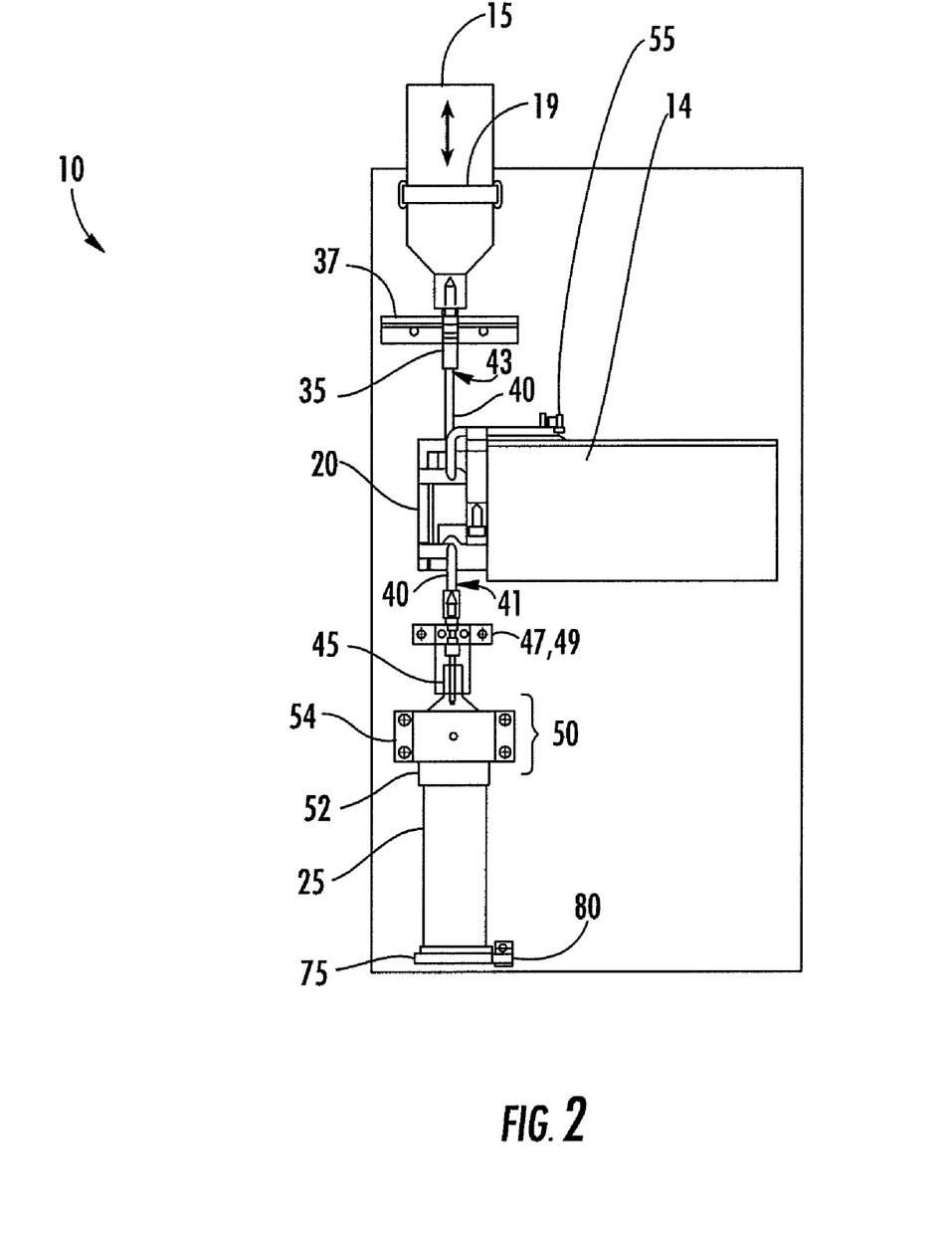
FIG. 2 is an exemplary schematic illustration of a syringe filling station of the present invention.
Figure 3:
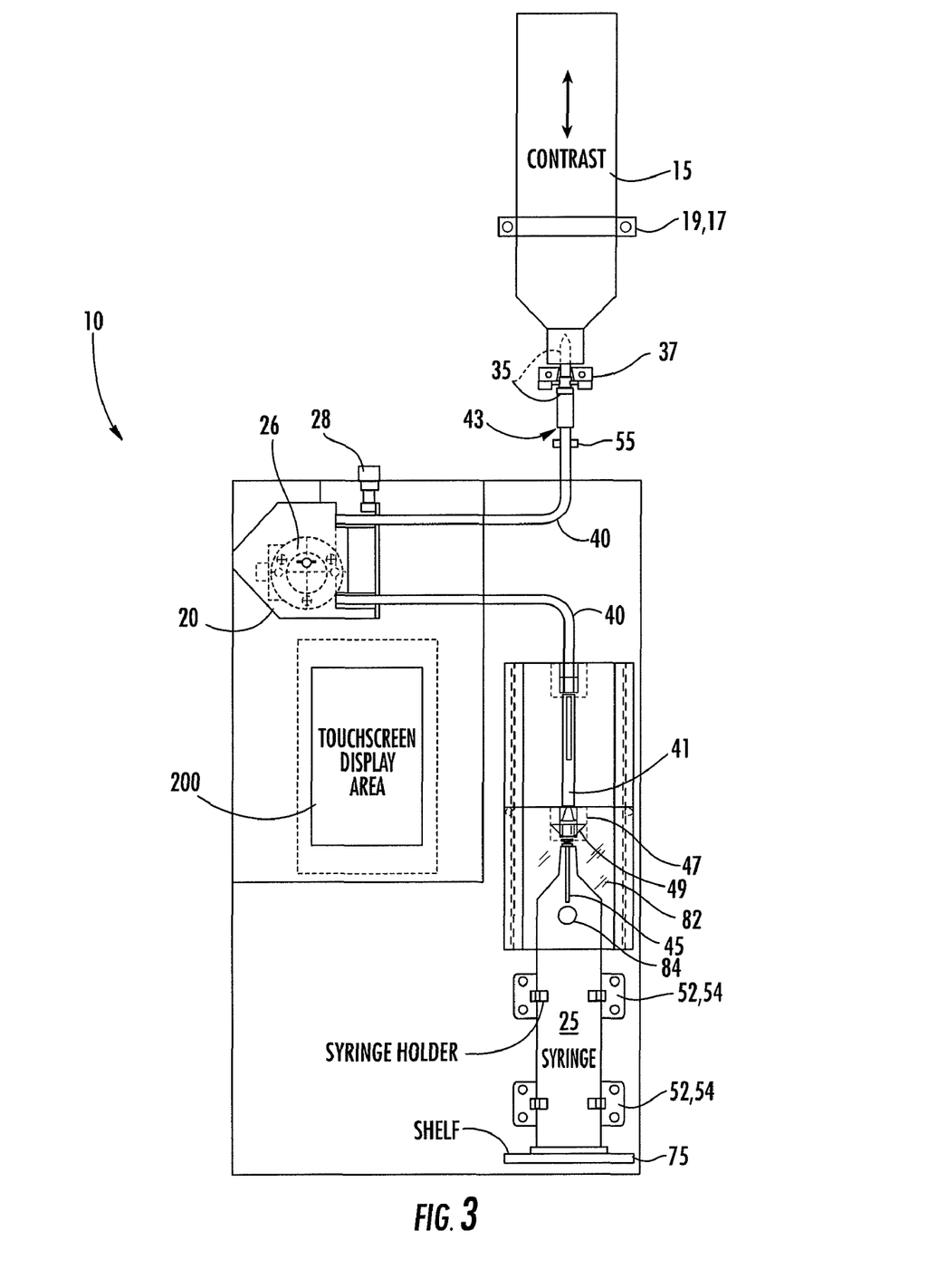
FIG. 3 is an exemplary schematic illustration of the syringe filling station depicted in FIG. 1 showing a pump.

In one embodiment, the filling station 10 includes a disposable fluid delivery system that transfers a fluid from the reservoir to the syringe. The fluid delivery system, also called an administration set or cartridge, is a consumable cartridge that can be replaced daily or at some other desirable time. With reference to FIGS. 2 and 3, a schematic illustration of a syringe filling station is shown. The fluid delivery system may includes a projecting member 35, which may include but is not limited to an outwardly projecting member, such as a spike, for example, flexible tubing 40, and a canula 45. The spike 35 can be inserted into a reservoir 15. The spike is attached to the upper or distal end 43 of the flexible tubing. The lower or proximal end 41 of the tubing 40 is attached to the canula 45. The fluid delivery system defines a path through which a fluid can travel from a reservoir to a syringe. In one embodiment, the fluid administration set is installed into the syringe filling station before the reservoir or syringe.

Figure 6:
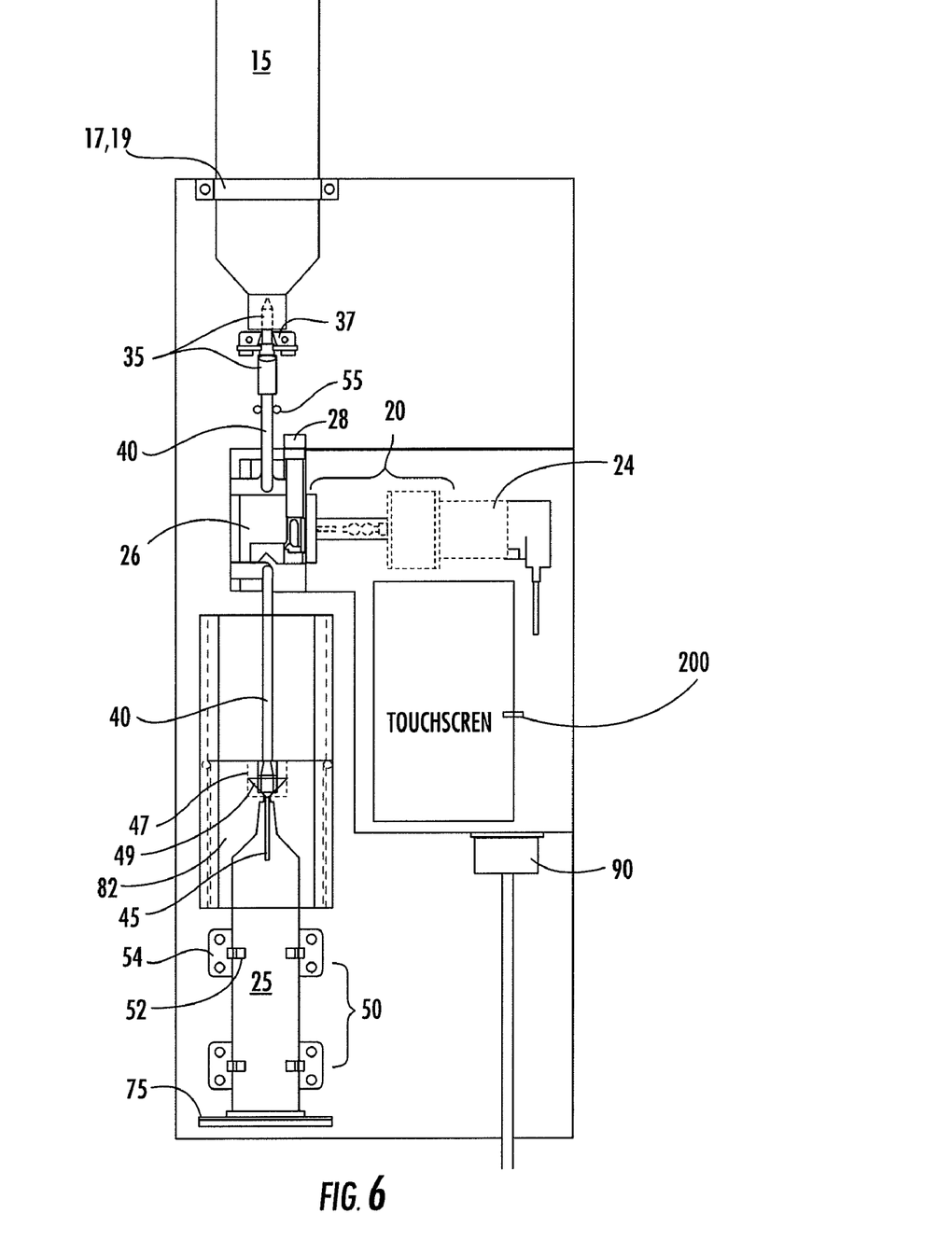
FIG. 6 is an exemplary schematic illustration of a syringe filling station of the present invention depicting a pump motor.

As shown in FIGS. 2, 3, and 6, the spike can be inserted into the reservoir. The spike is the entry point whereby fluid can enter the administration set and be moved to a syringe. The spike can be vented to allow for the passage of air into the reservoir as fluid is pumped out of the reservoir. The vent may be only one-way so that air cannot exit the reservoir through the vent. The vented spike can be filtered or non-filtered. The spike can be inserted into a standard rubber stoppered bottle or bag, for example. The spike can be supported by a spike locking mechanism or support collar 37. The spike support collar 37 is typically disposed adjacent to the reservoir 15. The spike support collar supports the spike and prevents the spike from shifting positions within the reservoir, or accidentally becoming disengaged from the reservoir. After depletion of the reservoir, the emptied reservoir can be easily detached from the spike, and a new reservoir can be attached and connected to the spike with little, if any, physical handling of the spike. As a result, possible contamination may be reduced or limited so that the syringe filling station provides an aseptic environment for syringe filling.

The flexible tubing may extend from the spike 35 to the canula 45. The tubing may define a fluid pathway through the filling station. Fluid can be moved through the tubing using a pump that applies pressure in a peristaltic fashion to the tubing. The flexible tubing may be composed of any suitable polymeric material so long as the material is flexible, durable, and suitable for medical use.

The canula 45 is disposed in close proximity to the syringe retaining guide. The canula typically may have a large bore. FIGS. 2 and 3 illustrate a guiding mechanism for securely positioning the canula so that it will be positioned in the center of the syringe. As stated above, the canula is typically attached to the lower end of the tubing 40. The canula can be positioned with a canula mount 47 and a canula guide 49 that are secured to a canula mount housing 53. The mount housing 53 ensures that the centerline of the syringe opening is coincident with the centerline of the canula. The canula mount 47 and guide 49 can position the canula so that upon insertion of a syringe, the canula will be centered within the syringe (see FIG. 7). As a result, the syringe may be easily inserted and aligned within the syringe filling station. In an alternate embodiment, the canula 45, canula mount 47, and canula guide 49 can be raised and then lowered into a syringe that has been pre-positioned within syringe retaining guide. In this regard, FIG. 3 illustrates a canula 45a in a raised position above a syringe 25. Once the syringe has been inserted into the retaining guide, the canula 45a is lowered into the syringe. A linear slide 51 (represented by the dashed lines) can lower and raise the canula 45. The linear slide is typically lowered or raised using a manual or mechanical mechanism. The syringe filling station can also include a clear viewing window 82 through which an operator can view syringe installation and canula placement. The canula guide and viewing window help to prevent contamination at the point of interface between the canula and the syringe tip. As a result, possible contamination may be limited and an aseptic environment can be maintained while changing and filling syringes.

Figure 4:
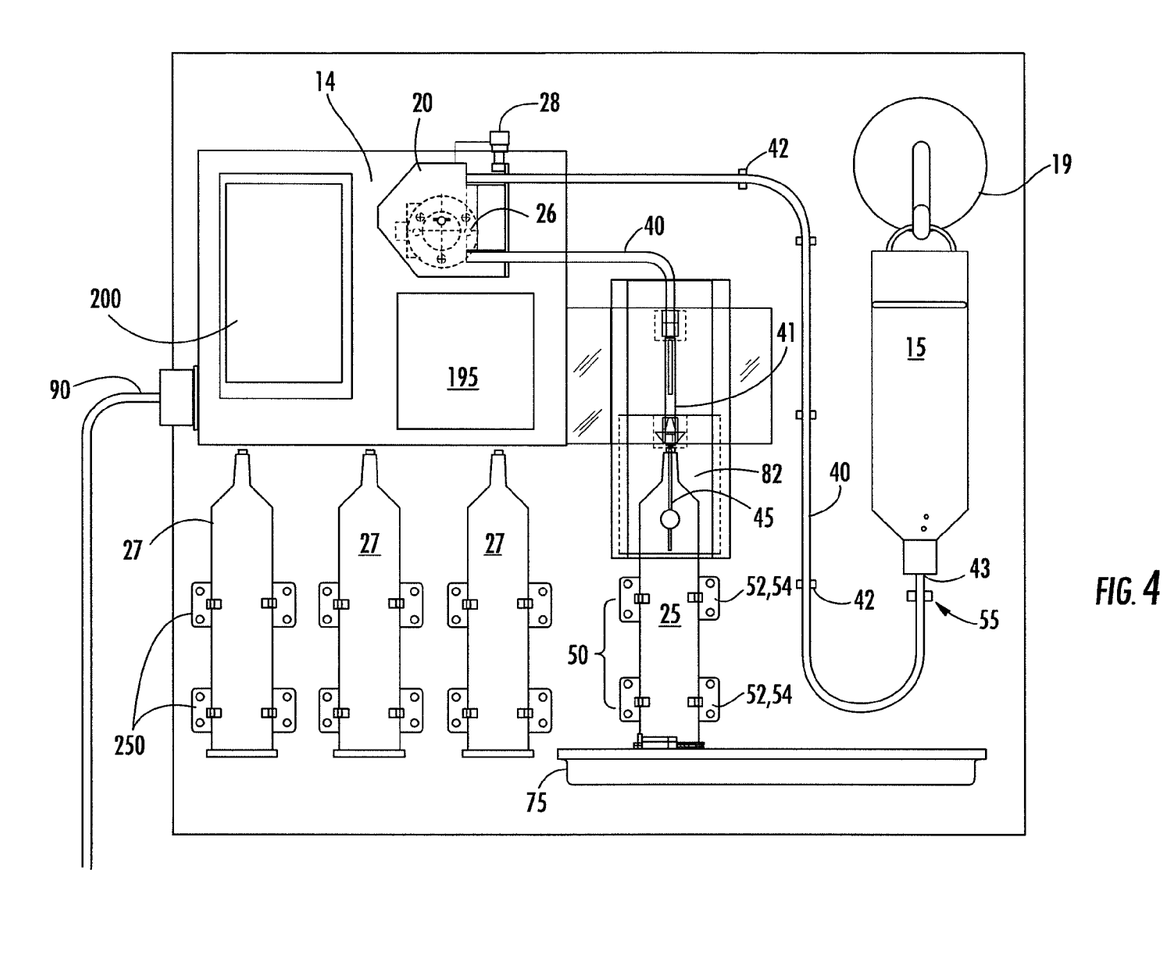
FIG. 4 is an exemplary schematic illustration of a syringe filling station adapted for a reservoir in the form of a bag.
Figure 5:
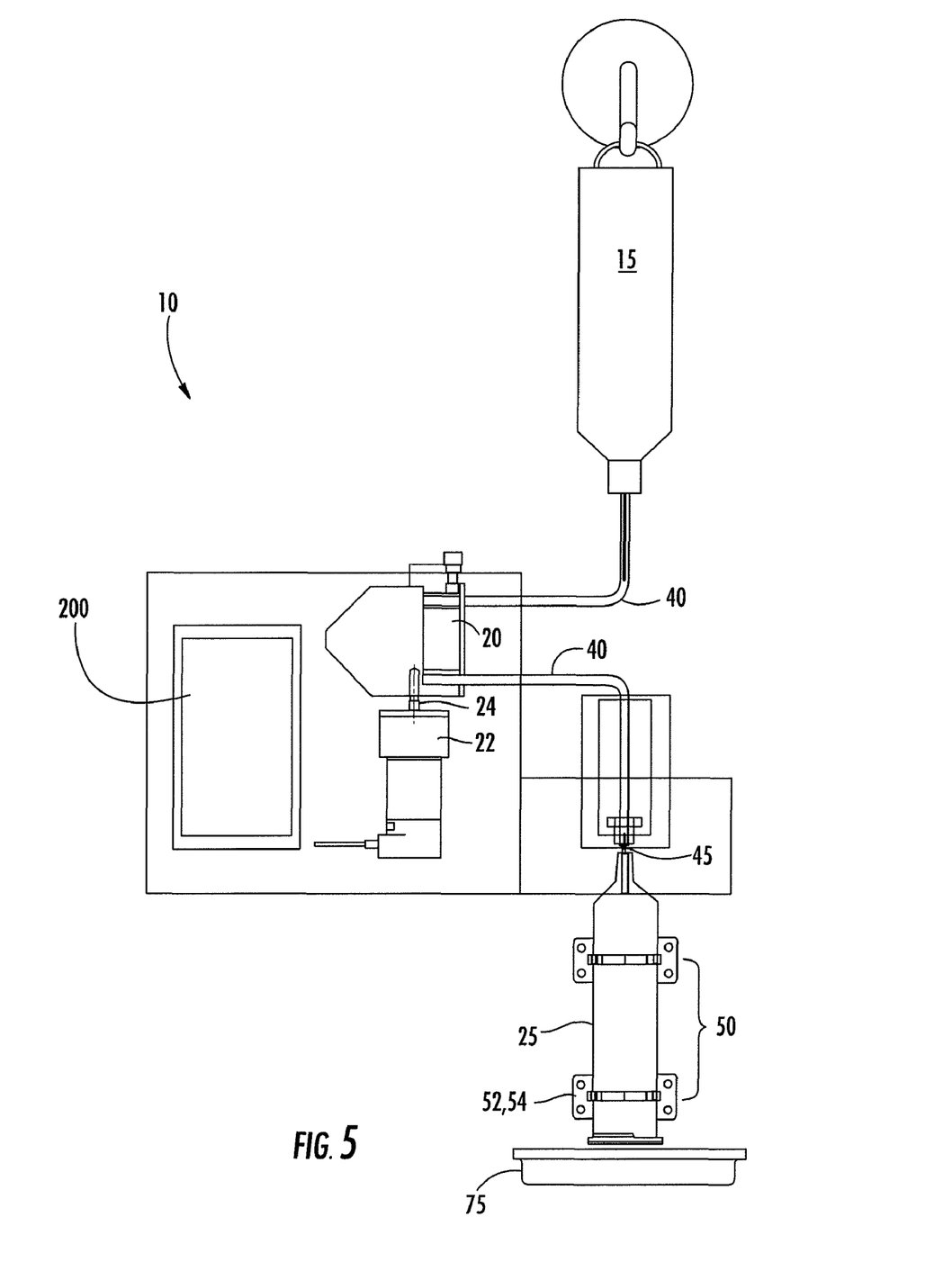
FIG. 5 is an exemplary schematic illustration of a syringe filling station of the present invention.

The reservoir can be attached to the filling station in a wide variety of manners. The reservoir attachment should securely position the reservoir, while still allowing the reservoir to be easily removed. As shown in FIG. 1, the housing can contain an inlet 17 adapted for removably receiving and connectingly attaching the reservoir 15. The reservoir can also be secured to the housing with a strap, bracket, sleeve, hook, hanger, or the like, that can removably receive the reservoir. FIGS. 4 and 5 illustrate a reservoir that is supported and positioned with a reservoir attachment 19 that is comprised of a hanger or hooking mechanism for supporting the reservoir. The reservoir attachment can also include a support pole for securing the bag.

Figure 7:
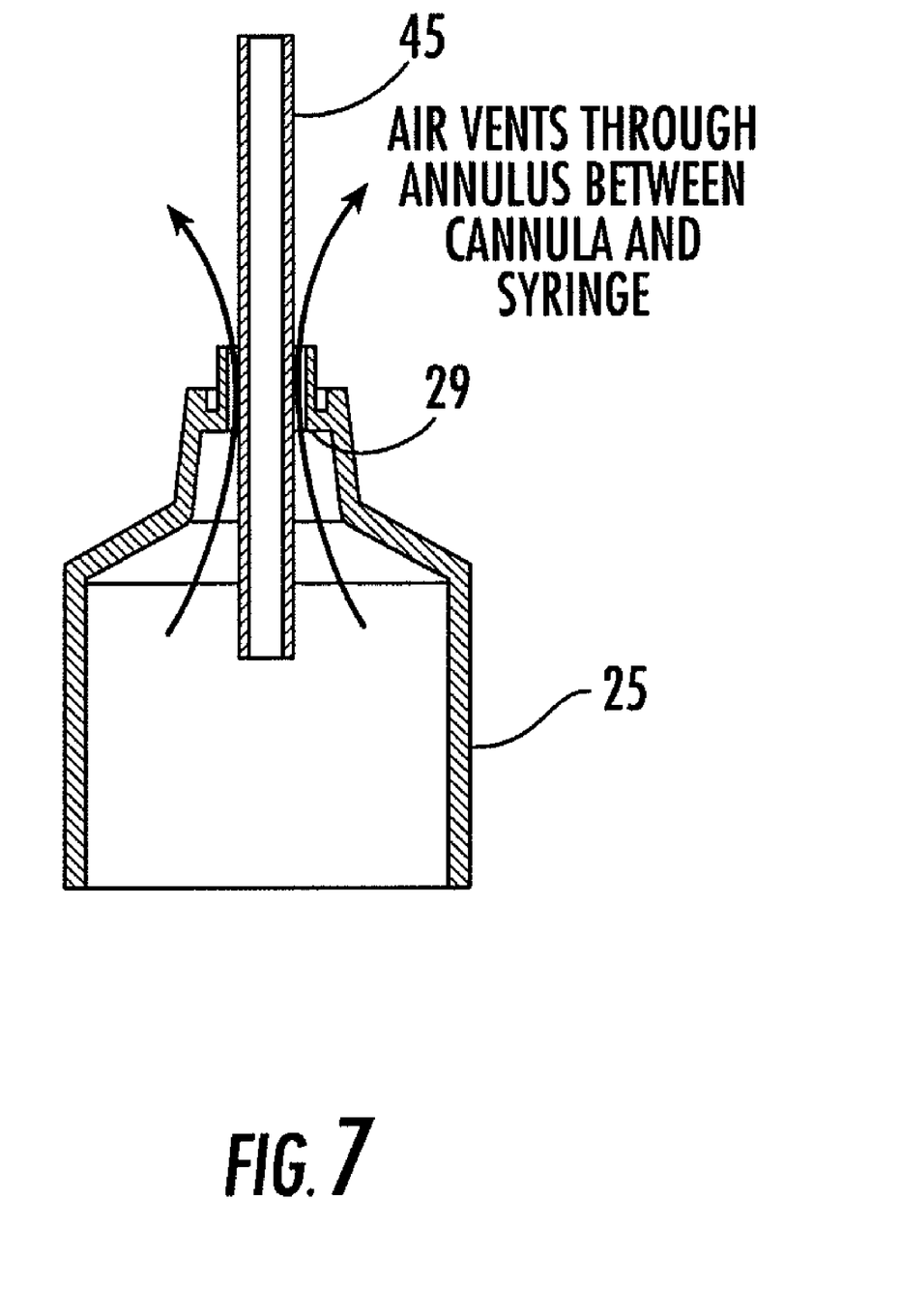
FIG. 7 is an exemplary schematic illustration depicting a canula partially inserted into a syringe.

In another embodiment of the present invention, the syringe retaining guide releasably retains the syringe within the filling station. The syringe retaining guide is adapted to positionally secure the syringe within the filling station and to serve as a guide for aligning the syringe with the canula 45. Preferably, the syringe retaining guide is adapted to securely lock the syringe in the filling station after it has been installed by an operator. In FIG. 2, a syringe retaining guide 50 is illustrated that is comprised of a guiding sleeve 52 and a gripping clip or clamp 54 that can grip and secure the syringe. The guiding sleeve 52 directs the syringe into the filling station so that the canula 45 enters the syringe without touching the inner sidewalls of the syringe. Preferably, the guiding sleeve directs the syringe into the retaining guide so that the canula is also centered within the syringe. The syringe should be positioned within the filling station so that the canula at least partially enters the syringe. The canula should be inserted into the syringe to an extent that prevents spillage of fluid, while still allowing the syringe to be filled and the escape of air from within the syringe. FIG. 7 illustrates a canula 45 that is partially inserted into the syringe 25. During the filling process, air can escape from within the syringe through small passageways 29 that exist between the inner wall of the syringe 25 and the canula 45. The syringe retaining guide 50 can also include brackets, straps, clips, or the like to releasably secure the syringe. In this regard, FIGS. 3 and 5 illustrate a filling station having two different types of syringe retaining guides that are used to releasably retain the syringe. Typically, the retaining guide will apply pressure to the barrel of the syringe to securely hold the syringe. The retaining guide 50 can also include a syringe support shelf 75 to support the syringe. The shelf can optionally include a pivot member 80 that allows the shelf to pivot about the pivot member. The shelf can also be slidably repositioned. As a result, the shelf can be conveniently moved so that the syringe can be easily inserted into, or withdrawn from, the syringe retaining guide.

The filling station can also include a clear plastic shield 82 that covers the canula 45. The shield allows an operator to view the insertion of the syringe into the filling station without contaminating the sterile syringe or administration set.

In one embodiment, the fluid pump 20 is used to pump fluid from the reservoir, through the tubing 40 to the canula 45 where it can be dispensed into a syringe. As shown in FIG. 5, the fluid pump 20 may include a peristaltic device 20 having a motor 22, shaft 24, and a rotatable peristaltic head 26 (see FIG. 3) that applies a pumping pressure to the tubing. In one embodiment, the peristaltic pump can be linear, rotational, or circumferential peristaltic pump. In one embodiment, a DC gear head motor 22 can drive the peristaltic head. In yet another embodiment, the motor is operatively connected to a control unit or processor. The processor may ramp up or ramp down motor speed. Controlling motor speed allows the pumping station to accurately fill a syringe with a desired amount of fluid. The peristaltic device can operate at both constant and variable rates. The fluid pump, control unit, power supply, and processor are normally contained within the housing. As shown in FIG. 2, a removable enclosure 14 covers and encloses the pump and control unit. Power is typically supplied to the pump and control unit with an electric power cord (see FIG. 4, reference number 90). In one embodiment, the pump can move fluid from the reservoir to the syringe without the use of an additional pressure pump.

As shown in FIG. 3, the fluid pump 20 also contains a tightening mechanism 28 that can be loosened to thread the tubing into the pump and around the peristaltic head 26. As shown in FIG. 3, the tightening mechanism can be a thumb screw that can be easily manipulated. It should be recognized, that the tubing can be secured using a variety of different mechanisms and fasteners. In an alternative embodiment, a lever mechanism for hand operation, or some electro-mechanical mechanism could be used to open and close the geometric gap between the rollers and stator belonging to the peristaltic pump 20 for purposes of loading and unloading the tubing 40. It is also envisioned that any mechanism or apparatus used to open and close that portion of the peristaltic pump 20 that interfaces with the tubing could include geometric features and attributes to facilitate loading and unloading of tubing. Such geometric features and attributes could similarly interface with some intermediate component attached to or mounted on the exterior of the tube to ease loading and unloading of the tube into the peristaltic pump. Such an arrangement could be as simple as an alignment tap or as complex as a cartridge enclosing the tube that in turn adapts to the peristaltic pump.

The fluid reservoir may contain a wide variety of different fluids such as contrast medias, flushing agents, fluid medications, among others. The syringe filling station is particularly useful for filling syringes with fluids that are used in CT injectors, such as a contrast medium. The fluid reservoir can have the form of a bottle, bag, pouch, container, or the like. The reservoir can also come in a variety of sizes. Typical reservoir volumes can range from about 10 to 1000 cc, with volumes from about 50 to 500 cc being somewhat more preferred. For example, iodinated contrast that is injected to the patient via a CT injector is routinely dispensed in bottles and bags within this range.

Figure 8:
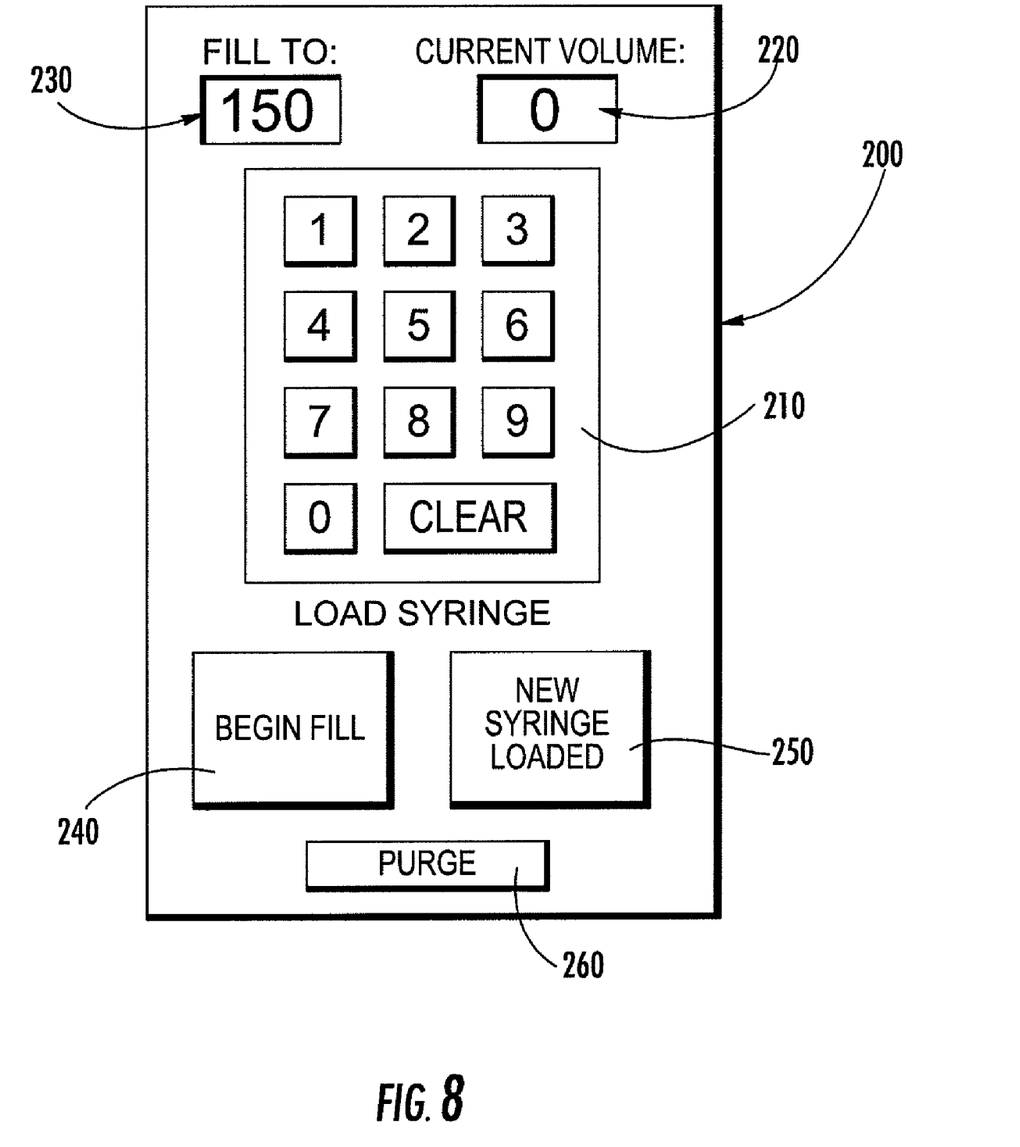
FIG. 8 is an exemplary, graphic illustration depicting a touchscreen of the present invention.

The syringe filling station can include a user interface that an operator can use to control the filling station. Typical command functions that can be entered with the interface include, but are not limited to, Fill volume, New syringe, Begin Fill, Pause, Stop, and Purge. An operator can use the interface to specify the amount of fluid to be dispensed into the syringe. In one embodiment of the present invention, the user interface can be in the form of a touchscreen that allows an operator to input commands. The touchscreen may be incorporated into a PC system that is in communication with the filling station or can be disposed on the filling station housing. In some embodiments, the syringe filling station can be in communication and operatively controlled from a remote interface that could be hosted or displayed, for example, on an injector user interface. The syringe filling station controls could be hosted entirely or partially on an external user interface. In this regard, FIG. 3 illustrates that the syringe filling station can include an input/output (I/O) terminal 202 for wired or wireless communication. FIGS. 3 through 6 illustrate a touchscreen 200 that is disposed on the outer surface of the housing 12. FIG. 8 illustrates an exemplary touchscreen 200 that can be used to operate the filling station. The touchscreen 200 can include several dedicated commands for filling a syringe. The interface can include a dedicated keyboard 210, or could alternatively include "up" or "down" arrows to vary the volume of fluid dispensed into the syringe. The user interface also includes displays for indicating current syringe volume 220 and the volume to be dispensed 230. The touchscreen 200 can include dedicated command functions such as "Begin Fill" 240, "New Syringe Loaded" 250, and "Purge" 260. The user interface can contain additional or different dedicated buttons than are described in FIG. 8. In an alternative embodiment, the user interface could be incorporated into an existing injector interface, such as an E-Z-EM Empower CT Remote Control, for example. Alternatively, the syringe filling station data interface could be in communication and operatively connected to an external or remote interface, such as an imaging equipment apparatus or other medical information IT system deployed within an imaging system or hospital. As shown in FIG. 3, the syringe filling station in some embodiments can include an I/O port or data interconnection 202 that can be in communication with an external control system or network. The data interconnection can be wired or wireless. An external interface could be used to input operation commands into the syringe filling station. For example, the external interface could be used to automatically specify syringe fill volumes on a per patient basis. This could help facilitate the tracking of patients electronically through the medical care process. Additionally, such data/control capability could be used to produce hardcopy information from a printing device. Such hardcopy data, particularly in the form of a printed label could be affixed to the syringe for identification purposes as it is removed from the syringe filling station and subsequently handled through injection to the patient. For example, valuable identifying information that could be printed on a label could include, but is not limited to: Date, Time, Person Filling, Patient Name, Patient ID Number, Medical Name of Fluid Filled in Syringe, Brand Name of Fluid Filled in Syringe, Lot Number of Fluid Filled in Syringe, Volume Filled in Syringe, Warnings, Cautions, and the like, and combinations thereof. In some embodiments, an OEM printer could be incorporated into the syringe filling station to provide readily accessible printed labels having the above described information.

The filling station may have a control unit for performing operations. In this regard, FIG. 4 illustrates a syringe filling station having a control unit 195. The control unit 195 typically includes a microprocessor that is incorporated into the filling station. The processor can be in communication with the user interface 200 and various sensors. The control unit may include computer code or programs for controlling the filling station and processing information and data received from a user interface, pump, or various sensors. The processor is also operatively connected to pump 20. In one alternative embodiment of the present invention, the processor can precisely control the pump so that a precise amount of fluid is delivered to the syringe. The pump and processor are normally in communication with each other. The pump can send data, such as pump speed, pumping revolutions, etc, to the processor that can allow the processor to accurately calculate and measure the amount of fluid that has been dispensed into the syringe. In one embodiment, the pump motor can include an encoder. In this embodiment, the volume delivered to the syringe may be measured by counting the pulses of the encoder. During use, the processor will measure the amount of fluid that has been dispensed into the syringe. The processor may also compensate for any air that could be in the administration cartridge. The processor can also optionally contain programmable code that can be used to perform routine system functions and filling operations that are used frequently. For example, if a particular dispensing volume is repeatedly used, the processor can be programmed to deliver a set volume of fluid without requiring the operator to input new fill levels for each new syringe.

When a new administration cartridge is installed into the syringe filling station, the interface may be used to manually or automatically instruct the pump to purge air contained within the tubing.

In another embodiment of the present invention, the filling station may also include sensors that are in communication with the processor and can monitor system status. Such sensors include an air in-line sensor or reservoir empty sensor, a sensor that detects when a new syringe is loaded into the filling station, a sensor for detecting the presence of an administration cartridge, and a sensor for detecting when a new reservoir has been added. The sensors can be used to optimize the performance and efficiency of the syringe filling station.

The air in-line sensor can detect the presence of air in the tubing or the depletion of fluid within the reservoir. The sensor 55 is normally disposed between the reservoir 15 and the pump 20. As shown in FIGS. 2 and 3 the sensor 55 can be disposed adjacent to the reservoir. The tubing 40 may pass through the sensor 50. If a pocket or bubble of air enters into the tubing and travels pass the sensor 50, the sensor can send a signal to the processor indicating the presence of air in the tubing or that the reservoir is depleted. If the sensor detects that the reservoir is depleted, the processor can direct the interface or remote control to display a message that the reservoir is emptied. In one embodiment, operation will not remove until the message has been removed.

Figure 9:
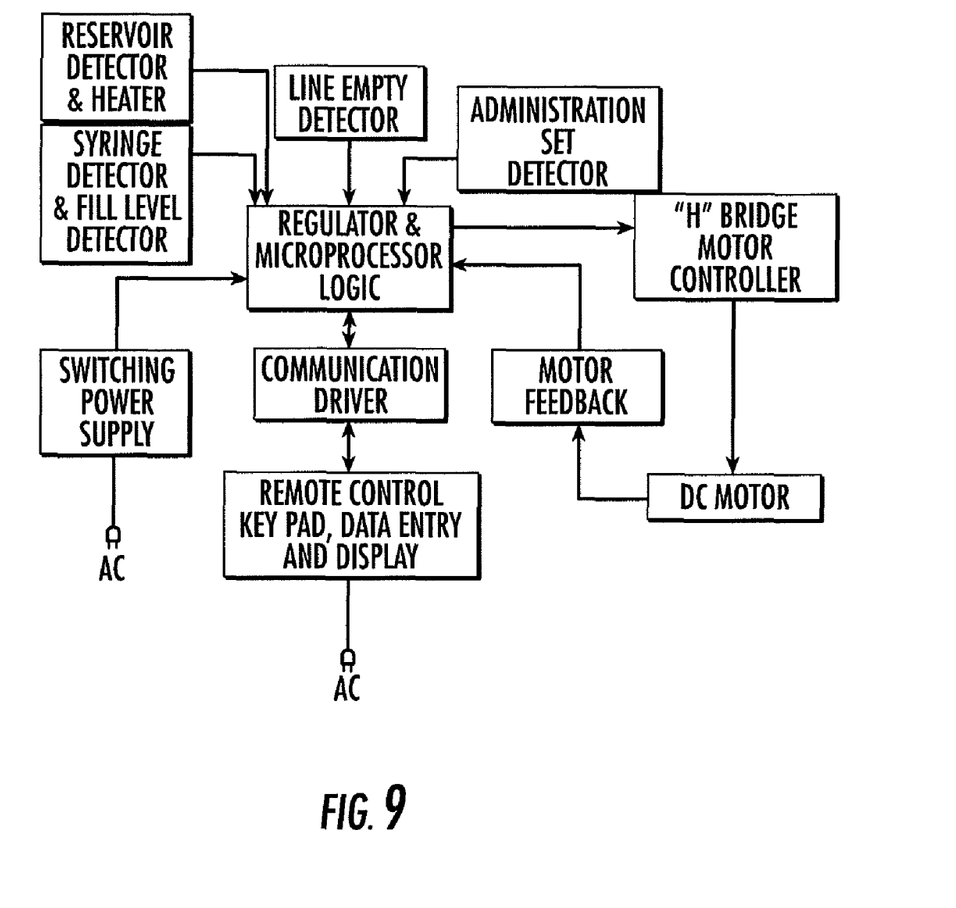
FIG. 9 is an exemplary, block diagram illustrating an electrical design schematic of an embodiment of the filling station.

With reference to FIG. 9, an electrical design schematic of one embodiment of the syringe filling station is illustrated. As shown in FIG. 9, the processor performs a variety of functions and is operatively connected to many sensors and devices. The processor can also be in communication with a remote control interface, such as a PC display or other computational CPU that can be used to input commands into the syringe filling station.

The processor can also automatically compensate for the volume of fluid that is needed to purge air from within the tubing. For instance, the processor will compensate for the air in the tubing after a new administration cartridge has been installed. The processor can also compensate for air that will be in the system after a new reservoir has been installed.

The system can also include a timing mechanism that can alert an operator that the administration cartridge needs to be changed. When an operator installs a new administration cartridge into the syringe filling station, a detector positioned within the housing 12, such as proximal to the syringe retaining guide, can detect the installation of the new cartridge. The sensor can send a signal to the control unit (processor) that a new cartridge has been installed. The processor can then start an internal timer that has been pre-programmed to alert the operator after a specified amount of time that the administration cartridge should be changed. The syringe filing station can also include a sensor to detect when a new syringe has been inserted into the syringe retaining guide. When a new syringe is detected, the processor can direct the interface to reset the syringe volume display to zero. The user interface can also include a command function whereby an operator could input that a new syringe has been installed.

The syringe filling station 10 can also include syringe storage holders 250 for removably storing filled syringes until they are needed. FIG. 4 illustrates a filling station 10 having a plurality of holding clips for storing filled syringes 27. The storage holders removably secure the filled syringes. The syringe storage holders can also include an optional heater (not shown) to heat the stored syringes 27 to a temperature that is comfortable for a patient. The filling station 10 can also optionally include a heater for heating the reservoir. The reservoir heater could heat the fluid to a temperature that is comfortable for a patient. The reservoir heater would allow the filled syringe to be used immediately after filling without having to further heat the syringe.

In one embodiment of the invention, the method of filling a syringe with a fluid comprises the steps of connecting a reservoir to a fluid administration cartridge, positioning a canula of the fluid administration cartridge at least partially in a syringe, and moving a fluid from the reservoir to a syringe using a peristaltic pump. In another embodiment, the operation of the syringe filling station can begin by installing an administration cartridge into the filling station. The tubing 40 is typically threaded around the pump. The lower end of the tubing, also referred to as the proximal end is connected to a fitting for the canula. The upper part of the tubing 40 is positioned in place using hold down clamps 42 and is threaded through the air in-line sensor 55. A reservoir is connected to the spike and the reservoir is then removably positioned using the reservoir attachment. A syringe is then inserted into the syringe retaining guide so that the canula is at least partially inserted into the syringe, and the syringe is releasably positioned within the filling station. The operator can then use the interface to specify a desired amount of fluid to dispense into the reservoir.

The following description illustrates some of the possible command functions that are available at the user interface. When a new administration cartridge is installed into the filling station, the control unit (processor) can automatically compensate for the volume of fluid contained within the cartridge. If a new reservoir is added, the control unit can compensate for the air in the line that can be present from the reservoir to the air in-line sensor. Alternatively, the interface can include a "PURGE" function to remove air from within the administration cartridge. In operation, a user can push and hold the PURGE button to operate the pump at a low speed to remove the air. After the system has been purged, the PURGE button may be released.

As stated above, the syringe retaining guide can also include a sensor to detect when a new syringe has been inserted. When a new syringe is inserted into the filling station the user interface can be programmed to display a reading indicating the insertion of a new syringe. An exemplary display could state, for example, "NEW SYRINGE LOADED." The operator could push this button to reset the Current Volume display. Alternatively, the control unit can be programmed to automatically reset the Current Volume to zero. For frequently repeated operations the control unit could store the syringe volume so that there would be no need to change the "FILL TO." However, an operator can still manually enter a desired fill volume. Typically, when the volume displayed in the "FILL TO" volume exceeds the "CURRENT VOLUME," a start button is enabled. The start button can display a command function such as "BEGIN FILL." The interface can also include command functions such as "CLEAR" to reset the fill volume.

In one embodiment, after the "BEGIN FILL" button has been activated by the operator, the pump will begin operating. The interface can include a "PAUSE" command function that can halt the operation. In yet another embodiment, touch-screen or input buttons can have multifunctions depending on the operation currently being carried out by the filling station. For example, if a touchscreen is being utilized, the "NEW SYRINGE LOADED" can be converted into a "PAUSE" button after pumping operations have started. During syringe filling, the CURRENT VOLUME" display can show the amount of fluid dispensed in real time. Additionally, if the "PAUSE" button has been pushed, the "BEGIN FILL" button can be reset to display a "RESUME FILL" button. After the specified volume has been dispensed, the control unit will stop the pump, and an "ADD MORE" button can be displayed to give an operator the opportunity to dispense additional fluid into the syringe. It should be recognized that the above examples are only exemplary of some of the command functions that can be incorporated into the control unit and the user interface.

From the foregoing discussion, it should be evident that the invention provides an apparatus and method that can be used to efficiently and accurately fill a syringe with a desired amount of fluid. The syringe filling station can include a user interface that allows an operator to easily control the amount of fluid dispensed into the syringe.

Figure 10:
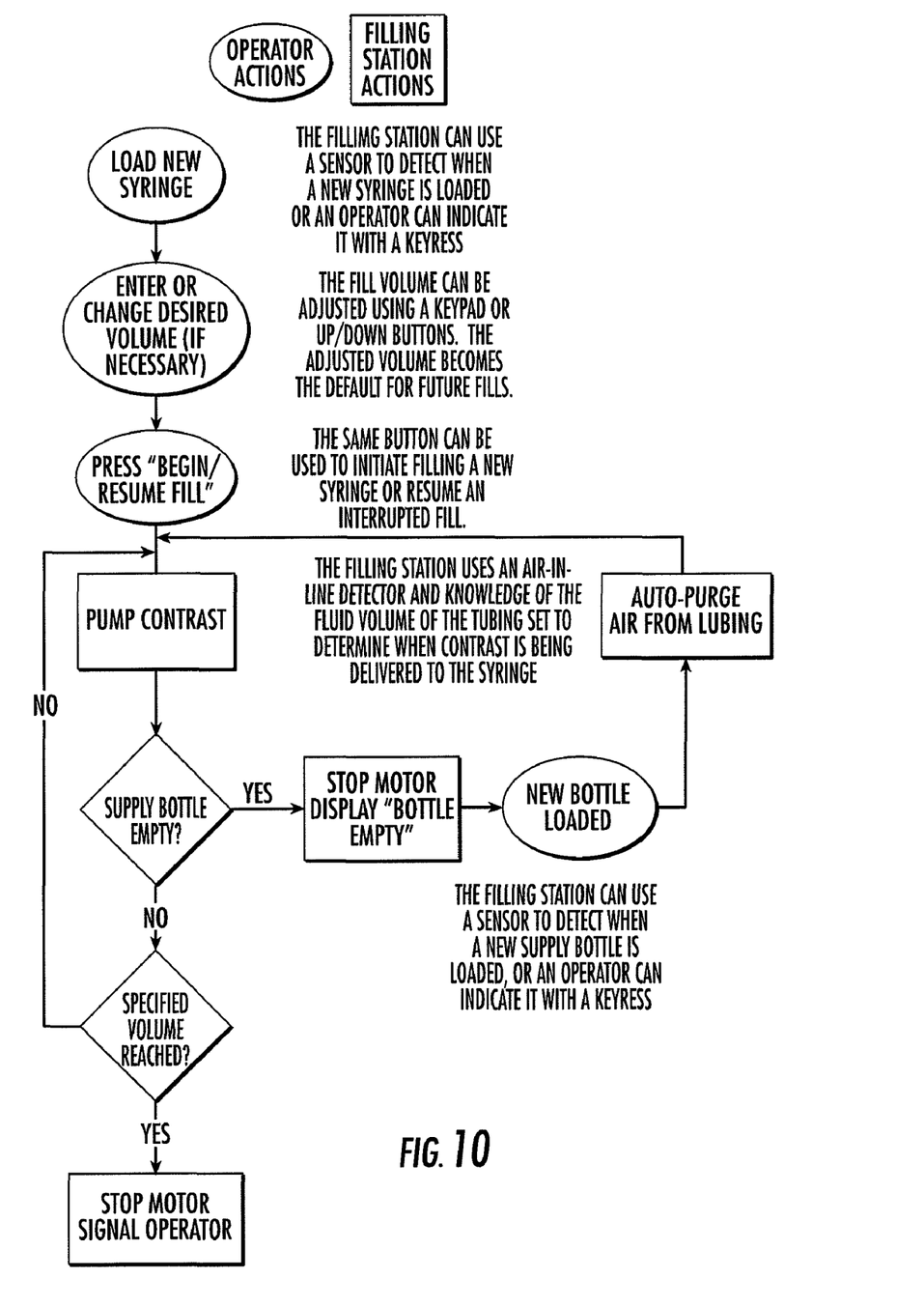
FIG. 10 is an exemplary, flow diagram describing a process for filling a syringe that is in accordance with the invention.
Figure 11:
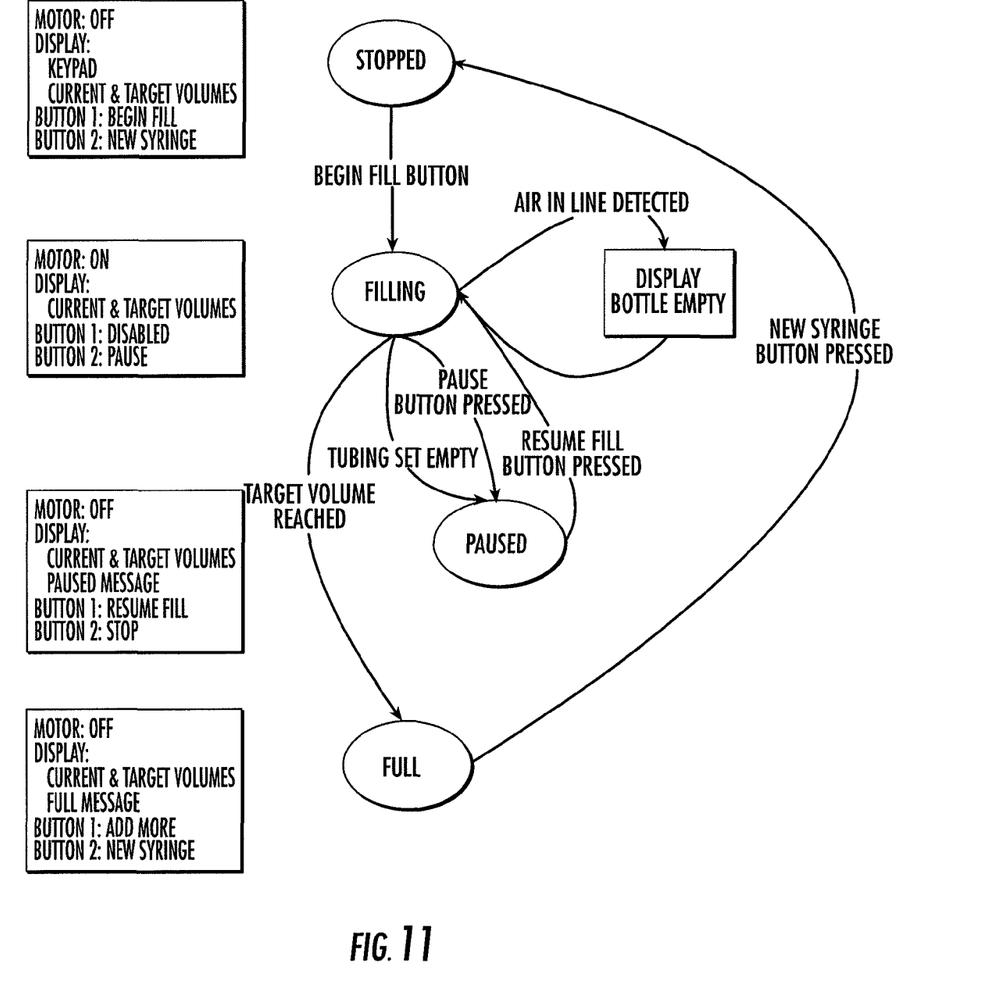
FIG. 11 is an exempting flow diagram correlating syringe filling operations with possible functions that could be displayed on the user interface.

FIGS. 10 and 11 illustrate flow diagrams describing possible steps the syringe filling station can take in filling a syringe. FIG. 10 depicts possible process steps that might occur in filling the syringe. In particular, FIG. 10 illustrates possible functions that may be available at each step of the process. FIG. 11 correlates the operations being performed by the syringe filling station with pump status and possible command functions that may be available at the user interface. It should be recognized that different and additional command functions and operations are possible, and that the invention is not limited to any specific set of commands or operations.

In one exemplary embodiment, the syringe filling station is adeptly suited for receiving and filling syringes with a contrast medium that is useful in medical imaging and diagnostic testing. Such diagnostic imaging includes, but is not limited to, CT, NMR/MRI, Ultrasound, Fluoroscopy, PET, and the like. Injection syringes for performing diagnostic testing typically have volumes from about 10 to 500 cc, with a volume from about 50 to 400 cc being somewhat more typical. Preferably, the syringe volume is from about 100 to 200 cc. Syringe length is typically from about 2 to 30 cm, and syringe diameter is typically from about 0.2 to 5 cm.

Modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. Also, the invention may suitably comprise, consist of or consist essentially of the elements described herein, and the elements described herein may be practiced in the absence of any element which is or is not specifically disclosed herein.

Throughout the description, where embodiments are described as having, including, or comprising specific components, or where methods are described as having, including, or comprising specific steps, it is contemplated that embodiments of the present invention also consist essentially of, or consist of the recited components, and that the methods of the present invention also consist essentially of, or consist of the recited method steps. Further, it should be understood that the order of steps or order for performing certain actions may vary and need not be performed pursuant to a specific non-varying sequence so long as the invention remains operable. Moreover, two or more steps or actions may be conducted simultaneously.

We claim:

1. A method of filling a syringe with a fluid comprising:
   a) connecting a reservoir to a fluid administration cartridge;
   b) detecting the administration cartridge;
   c) positioning a canula of the fluid administration cartridge at least partially in a syringe; and
   d) moving a fluid from the reservoir to a syringe using a peristaltic pump.

2. A method of filling a syringe according to claim 1, further comprising the step of positioning the syringe on a movable support shelf.

3. A method of filling a syringe according to claim 1, further comprising the step of specifying an amount of fluid to move to the syringe.

4. A method of filling a syringe according to claim 3, wherein specifying an amount of fluid to dispense includes a user interface to input the amount of fluid.

5. A method of filling a syringe according to claim 1, further including the step of purging air from the administration cartridge.

6. A method of filling a syringe according to claim 1, further including the step of compensating for air in the administration cartridge.

7. A method of filling a syringe according to claim 1, further including the step of measuring the amount of fluid that has been dispensed into the syringe.

8. A method of filling a syringe according to claim 7, wherein the step of measuring the amount of fluid includes a control unit.

9. A method of filling a syringe according to claim 8, wherein the pump and the control unit are in communication with each other.

10. A method of filling a syringe according to claim 1, further comprising the step of heating the fluid disposed in the reservoir.

11. A method of filling a syringe with a fluid comprising:
    a) providing a filling station having a reservoir attachment for removably receiving a reservoir, a fluid pump, and a syringe retaining guide, the syringe retaining guide being configured to releasably secure a syringe to the filling station;
    b) providing a consumable administration cartridge comprising a projecting member for inserting into a reservoir, a flexible tubing having a distal end attached to the projecting member, and a canula attached to the proximal end of the flexible tubing, said canula adapted for at least partial insertion into a syringe
    c) installing the administration cartridge into the filling station to define a fluid pathway from the reservoir attachment to the syringe retaining guide;
    d) connecting a fluid reservoir to the reservoir attachment;
    e) inserting a syringe into the retaining guide so that at least a portion of the canula is partially inserted into the syringe; and
    f) pumping the fluid from the reservoir into the syringe.

12. A method of filling a syringe according to claim 11, wherein the step of pumping the fluid further includes the step of inputting a specified volume of fluid to pump into a user interface.

13. A method of filling a syringe according to claim 12, further comprising communicating the specified volume to a control unit.

14. A method of filling a syringe according to claim 13, further including sending commands from the control unit to the pump, whereby the pump moves a specified volume of fluid from the reservoir to the syringe.

15. A method of filling a syringe according to claim 11, further comprising the step of detecting air in the fluid delivery system.

16. A method of filling a syringe according to claim 15, further comprising the step of purging air from the delivery system.

17. A method of filling a syringe according to claim 13, further including the step of displaying the volume of fluid moved to the syringe.

18. A method of filling a syringe according to claim 13, further comprising calculating the volume of fluid moved from the reservoir to said pump.

19. A method of filling a syringe according to claim 16, further comprising a processor for calculating the volume of fluid moved from the reservoir to the pump.

20. A method of filling a syringe according to claim 11, wherein the pump is a peristaltic pump.

* * * * *